(12) United States Patent
Yoda et al.

(10) Patent No.: US 8,306,271 B2
(45) Date of Patent: Nov. 6, 2012

(54) DROWSINESS ASSESSMENT DEVICE AND PROGRAM

(75) Inventors: Takumi Yoda, Seto (JP); Takuhiro Omi, Anjo (JP); Akira Kadoya, Kitanagoya (JP); Isahiko Tanaka, Susono (JP)

(73) Assignees: Aisin Seiki Kabushiki Kaisha, Aichi-ken (JP); Denso Corporation, Aichi-ken (JP)

( * ) Notice: Subject to any disclaimer, the term of this patent is extended or adjusted under 35 U.S.C. 154(b) by 0 days.

(21) Appl. No.: 13/257,182

(22) PCT Filed: Mar. 17, 2010

(86) PCT No.: PCT/JP2010/054563
§ 371 (c)(1),
(2), (4) Date: Sep. 16, 2011

(87) PCT Pub. No.: WO2010/107066
PCT Pub. Date: Sep. 23, 2010

(65) Prior Publication Data
US 2012/0002843 A1    Jan. 5, 2012

(30) Foreign Application Priority Data
Mar. 19, 2009   (JP) .................................. 2009-068281

(51) Int. Cl.
*G06K 9/00* (2006.01)
(52) U.S. Cl. ......... 382/104; 382/103; 382/107; 382/117
(58) Field of Classification Search .................. 382/103, 382/104, 107, 117, 118
See application file for complete search history.

(56) References Cited

U.S. PATENT DOCUMENTS

| | | | | |
|---|---|---|---|---|
| 5,878,156 A | * | 3/1999 | Okumura | 382/118 |
| 6,690,814 B1 | * | 2/2004 | Yuasa et al. | 382/118 |
| 7,599,524 B2 | * | 10/2009 | Camus et al. | 382/117 |
| 7,692,550 B2 | * | 4/2010 | Bonefas et al. | 340/575 |

(Continued)

FOREIGN PATENT DOCUMENTS

| | | |
|---|---|---|
| JP | 07-241283 A | 9/1995 |
| JP | 11-066304 A | 3/1999 |
| JP | 2004-041485 A | 2/2004 |
| JP | 2008-073335 A | 4/2008 |
| JP | 2009-028237 A | 2/2009 |

OTHER PUBLICATIONS

U.S. Appl. No. 13/383,085, filed Jan. 9, 2012, Koji Oguri.

*Primary Examiner* — Vu Le
*Assistant Examiner* — Aklilu Woldemariam
(74) *Attorney, Agent, or Firm* — Sughrue Mion, PLLC

(57) ABSTRACT

Local maxima values and local minima values are derived from eyelid openness time series data in a segment in which a continuous closed eye period of extracted blinks is a specific time duration (for example 1 second) or longer. When plural local minima values are present in the segment of continuous closed eye period of 1 second or longer, blinks are extracted passing over and back through each variable closed eye threshold value of a variable closed eye threshold that is slid in a direction from the derived local maxima value towards the local minima value in set steps to a low value, and a inter-blink interval derived. Determination is made that a blink burst has occurred when the derived inter-blink interval is 1 second or less, and say greater than 0.2 seconds, thereby detecting a blink burst. Blink bursts can be detected with good precision, and the state of drowsiness can be assessed with good precision.

9 Claims, 12 Drawing Sheets

U.S. PATENT DOCUMENTS 7,821,409 B2 * 10/2010 Ishida .......................... 340/576
2007/0014431 A1 * 1/2007 Hammoud et al. ........... 382/103
2008/0101659 A1 * 5/2008 Hammoud et al. ........... 382/118
2009/0027212 A1 1/2009 Nakagoshi et al.

* cited by examiner

FIG.2

| STATE TRANSITION | CONTENTS | POINT |
|---|---|---|
| OPEN → HALF → CLOSED, NORMAL MOVEMENT | | 1 |
| OPEN → HALF → OPEN, OPENING WHEN HALF-WAY THROUGH CLOSING | RETURNING FROM HALF-OPEN | 0 |
| OPEN → CLOSED, RAPID TRANSITION FROM OPEN TO CLOSED | OPEN TO CLOSE WITHOUT PRESENCE OF A HALF-OPEN STATE | 1 |
| CLOSED → HALF → OPEN, NORMAL MOVEMENT | | 1 |
| CLOSED → HALF → CLOSED, CLOSING WHEN HALF-WAY THROUGH OPENING | RETURNING FROM HALF OPEN | 0 |
| CLOSED → OPEN, RAPID TRANSITION FROM CLOSED TO OPEN | CLOSE TO OPEN WITHOUT PRESENCE OF A HALF-OPEN STATE | 1 |
| OPEN, KEPT OPEN | | 0 |
| HALF, KEPT HALF-OPEN | | 0 |
| CLOSED, KEPT CLOSED | | 0 |

DROWSINESS ASSESSMENT DEVICE AND PROGRAM

CROSS REFERENCE TO RELATED APPLICATIONS

This application is a National Stage of International Application No. PCT/JP2010/054563 filed Mar. 17, 2010, claiming priority based on Japanese Patent Application No. 2009-068281 filed Mar. 19, 2009, the contents of all of which are incorporated herein by reference in their entirety.

TECHNICAL FIELD

The present invention relates to a drowsiness assessment device and program, and in particular to a drowsiness assessment device and program for assessing the state of drowsiness of a vehicle driver.

BACKGROUND ART

There are known falling-arousal-level detection devices that determine from detected blinks any blinks of blink bursts that occur with an inter-blink interval within a specific time duration, and determine blinks accompanying a lengthy closed eye period of a specific duration or longer, so as to determine falling arousal level in an investigation subject from history data of blink burst blinks and blinks accompanying lengthy closed eye periods (see Patent Document 1). Japanese Patent Application Laid-Open (JP-A) No. 2008-73335

DISCLOSURE OF INVENTION

Technical Problem

However, blinks are extracted without splitting into normal blinks and blinks of blink bursts in the technology described in Patent Document 1, and the extraction method is not specialized for blink bursts. Accordingly a blink phenomenon often observed during blink bursts, in which an eye transitions from closed to half-open and then back to closed, cannot be detected, resulting in the issue that blink bursts cannot be detected with good precision.

In order to address the above issue, the present invention is directed towards providing a drowsiness assessment device and a program that can detect blink bursts with good precision, and can assess the state of drowsiness with good precision.

Solution to Problem

In order to achieve the above objective a drowsiness assessment device according to a first aspect of the present invention is configured including: image capture means that successively captures an image of a region including an eye of an assessment subject; openness detection means that detects time series data of eyelid openness based on the images successively captured by the image capture means; blink burst detection means that based on the eyelid openness time series data detected by the openness detection means extracts any local maxima values and local minima values from a range in which the eyelid openness is continuously less than a specific threshold value and detects blink bursts when an inter-blink interval detected at a threshold value set between an extracted local maxima value and an extracted local minima value is within a specific time duration; and state of drowsiness assessment means that assesses the state of drowsiness of the assessment subject based on the detection result of the blink burst detection means.

A computer program according to a second aspect of the present invention is a computer program comprising instructions that are executable by a computer to function as: openness detection means that detects time series data of eyelid openness based on images successively captured by an image capture means of a region including an eye of an assessment subject; blink burst detection means that based on the eyelid openness time series data detected by the openness detection means extracts any local maxima values and local minima values from a range in which the eyelid openness is continuously less than a specific threshold value and detects blink bursts when an inter-blink interval detected at a threshold value set between an extracted local maxima value and an extracted local minima value is within a specific time duration; and state of drowsiness assessment means that assesses the state of drowsiness of the assessment subject based on the detection result of the blink burst detection means.

According to the first and second aspects of the present invention, images are successively capture by the image capture means of a region including an eye of an assessment subject, and eyelid openness time series data is detected based on the images successively captured by the image capture means.

Then, based on the eyelid openness time series data detected by the openness detection means, the blink burst detection means extracts any local maxima values and local minima values from a range in which the eyelid openness is continuously less than a specific threshold value and detects blink bursts when an inter-blink interval detected at a threshold value set between an extracted local maxima value and an extracted local minima value is within a specific time duration. The state of drowsiness assessment means then assesses the state of drowsiness of the assessment subject based on the detection result of the blink burst detection means.

Extracting any local maxima values and local minima values from a range in which the eyelid openness is continuously less than the specific threshold value and detecting blink bursts using a threshold value set between the local maxima value and the local minima value enables blink bursts to be detected with good precision, and enables the state of drowsiness to be assessed with good precision.

Configuration may be made such that the specific threshold value is set as a standard closed eye threshold value related to eyelid openness.

Configuration may be made such that the blink burst detection means extracts any local maxima values and local minima values in a range of eyelid openness continuously less than the specific threshold value from a range of a second specific time duration or longer, and detects blink bursts when an inter-blink interval detected at a threshold value set between an extracted local maxima value and an extracted local minima value is within the specific time duration.

Configuration may be made such that the blink burst detection means extracts any local maxima values and local minima values respectively from plural extraction sections determined at a minimum unit duration from a range of eyelid openness continuously less than the specific threshold value and detects blink bursts when an inter-blink interval detected at a threshold value set between an extracted local maxima value and an extracted local minima value is within a specific time duration. Blink burst can accordingly be detected by setting the threshold value between the local maxima value and the local minima value for each of the extraction segments one at a time.

A drowsiness assessment device according to a third aspect of the present invention includes: image capture means that successively captures an image of a region including an eye of an assessment subject; openness detection means that detects time series data of eyelid openness based on the images successively captured by the image capture means; blink burst detection means that based on the eyelid openness time series data detected by the openness detection means extracts any local minima values from a range in which the eyelid openness is continuously less than a specific threshold value and detects blink bursts when an interval between extracted local minima values is within a specific time duration; and state of drowsiness assessment means that assesses the state of drowsiness of the assessment subject based on the detection result of the blink burst detection means.

A program according to a fourth aspect of the present invention is a program causing a computer to function as functions including: openness detection means that detects time series data of eyelid openness based on images successively captured by an image capture means of a region including an eye of an assessment subject; blink burst detection means that based on the eyelid openness time series data detected by the openness detection means extracts any local minima values from a range in which the eyelid openness is continuously less than a specific threshold value and detects blink bursts when an interval between extracted local minima values is within a specific time duration; and state of drowsiness assessment means that assesses the state of drowsiness of the assessment subject based on the detection result of the blink burst detection means.

According to the third and fourth aspects of the present invention, images are successively capture by an image capture means of a region including an eye of the assessment subject, and eyelid openness time series data is detected by the openness detection means based on the images successively captured by the image capture means.

Then based on the eyelid openness time series data detected by the openness detection means the blink burst detection means extracts any local minima values from a range in which the eyelid openness is continuously less than a specific threshold value and detects blink bursts when an interval between extracted local minima values is within a specific time duration. The state of drowsiness assessment means then assesses the state of drowsiness of the assessment subject based on the detection result of the blink burst detection means.

Extracting any local minima values from a range in which the eyelid openness is continuously less than a specific threshold value and detecting blink bursts based on an interval between extracted local minima values accordingly enables blink bursts to be detected with good precision, and enables the state of drowsiness to be assessed with good precision.

The above drowsiness assessment device may be configured further including second blink burst detection means that extracts blinks employing a specific threshold value based on the eyelid openness time series data detected by the openness detection means, and detects blink bursts based on the extracted blinks, wherein the state of drowsiness assessment means assesses the state of drowsiness of the assessment subject based on the detection result of the blink burst detection means and the detection result of the second blink burst detection means.

The above drowsiness assessment device may be configured further including blink characteristic amount extraction means that extracts a blink characteristic amount different from blink bursts based on the eyelid openness time series data detected by the openness detection means, wherein the state of drowsiness assessment means assesses the state of drowsiness of the assessment subject based on the detection result of the blink burst detection means and based on the blink characteristic amount extracted by the blink characteristic amount extraction means.

Advantageous Effects of Invention

As explained above, the drowsiness assessment device and the program of the present invention exhibit the excellent effects of enabling blink bursts to be detected with good precision, and enabling the state of drowsiness to be assessed with good precision.

BRIEF DESCRIPTION OF DRAWINGS

FIG. 2 is a table illustrating a relationship between transitions between open or closed eye states and points.

BEST MODE FOR CARRYING OUT THE INVENTION

Detailed explanation follows regarding exemplary embodiments of the present invention, with reference to the drawings. Examples of the present invention applied to a vehicle mounted drowsiness assessment device are explained.

Figure 1:
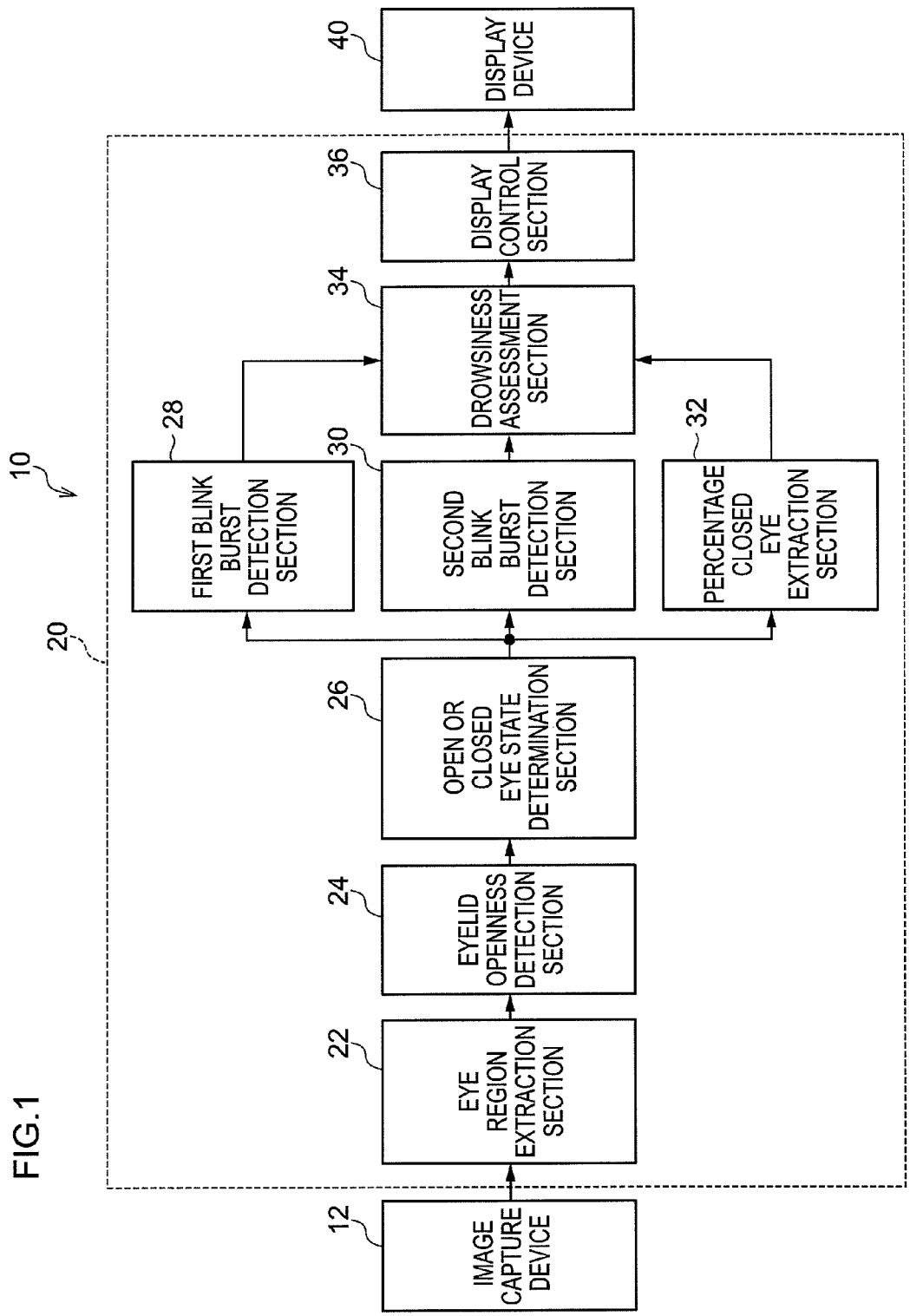
FIG. 1 is a schematic diagram illustrating a configuration of a drowsiness assessment device according to a first exemplary embodiment of the present invention.

As shown in FIG. 1, a drowsiness assessment device 10 according to a first exemplary embodiment is, for example, equipped with an image capture device 12 that is mounted diagonally in front of a driver acting as an assessment subject and captures successive images from diagonally below the face of the driver; and a computer 20 for performing state of drowsiness assessment based on the face images captured by the image capture device 12 and displaying the assessment result on a display device 40.

The computer 20 is equipped with a CPU, a RAM, and a ROM stored with a program for executing a threshold value calculation processing routine, a percentage closed eye extraction processing routine, a first blink burst detection processing routine, and a second blink burst detection processing routine, as described later, so as to configure the following functionality. The computer 20 is equipped with: an eye region extraction section 22 for extracting an eye region representing an eye of a driver from a face image; an eyelid openness detection section 24 for detecting and storing the eyelid openness indicating the degree by which the eyelids are open; an open or closed eye state determination section 26 that utilizes a preset closed eye threshold value and a preset open eye threshold value to determine an open or closed eye state of each eyelid openness from the detected eyelid openness time series data, and stores time series data of open or closed states; a first blink burst detection section 28 for detecting blink bursts (grouping) from stored open or closed eye state time series data; a second blink burst detection section 30 for detecting blink bursts from the stored time series data of open or closed eye states and time series data of eyelid openness; percentage closed eye extraction section 32 for extracting a percentage closed eye from stored open or closed eye state time series data; a drowsiness assessment section 34 for assessing the state of drowsiness based on the detection results of the first blink burst detection section 28 and the second blink burst detection section 30 and based on the percentage closed eye extracted by the percentage closed eye extraction section 32; and a display control section 36 for displaying warning information on the display device 40 when a strong state of drowsiness is assessed. The first blink burst detection section 28 is an example of second blink burst detection means of the present invention, and the second blink burst detection section 30 is an example of blink burst detection means of the present invention.

In the eyelid openness detection section 24, successive detection is made of the eyelid openness based on the proportion of the separation distance from the upper eyelid to the lower eyelid detected in the image of the eye region with respect to a predetermined separation distance between the upper eyelid and the lower eyelid when fully open, successively detects eyelid openness, and stores the eyelid openness time series data. The eyelid openness detection section 24 detects the eyelid openness when the eye is fully open as 100%, when closed as 0%, and as being, say, about 50% when in a half-open drowsy state. Configuration may be made such that the separation distance between the upper eyelid and the lower eyelid is detected as the eyelid openness.

The open or closed eye state determination section 26 utilizes a predetermined fixed closed eye threshold value and a predetermined fixed open eye threshold value to determine the open or closed eye state for each eyelid openness from the time series data of detected eyelid openness and store the open or closed eye state time series data. An open eye state is determined to exist when the eyelid openness is the fixed open eye threshold value or greater. However, a half-open state is determined to exist when the eyelid openness is the fixed closed eye threshold value or greater but less than the fixed open eye threshold value. A closed eye state is determined to exist when the eyelid openness is less than the fixed closed eye threshold value. The fixed closed eye threshold value and the fixed open eye threshold value are respectively a standard closed eye threshold value and a standard open eye threshold value related to eyelid openness and may be determined by any known method.

The first blink burst detection section 28 computes the number of eye blinks in the open or closed eye state time series data determined using the fixed closed eye threshold value and the fixed open eye threshold value. The first blink burst detection section 28 determines that a blink burst has occurred when, for example, the computed number of blinks in a fixed time interval, such as 1 second, is a given value or greater, thereby detecting a blink burst. The first blink burst detection section 28 adds together points allocated to each state transition, as shown in FIG. 2, each time a state transition occurs from state transitions of the open or closed eye states, and computes the number of blinks by dividing by two. A phenomenon is observed in which blinking is repeated plural times in succession within a short period of time when a person is feeling drowsy. This phenomenon is called a blink burst, and it is possible to assess the state of drowsiness with good precision if you know a blink burst has occurred in a given period of time.

Figure 3:
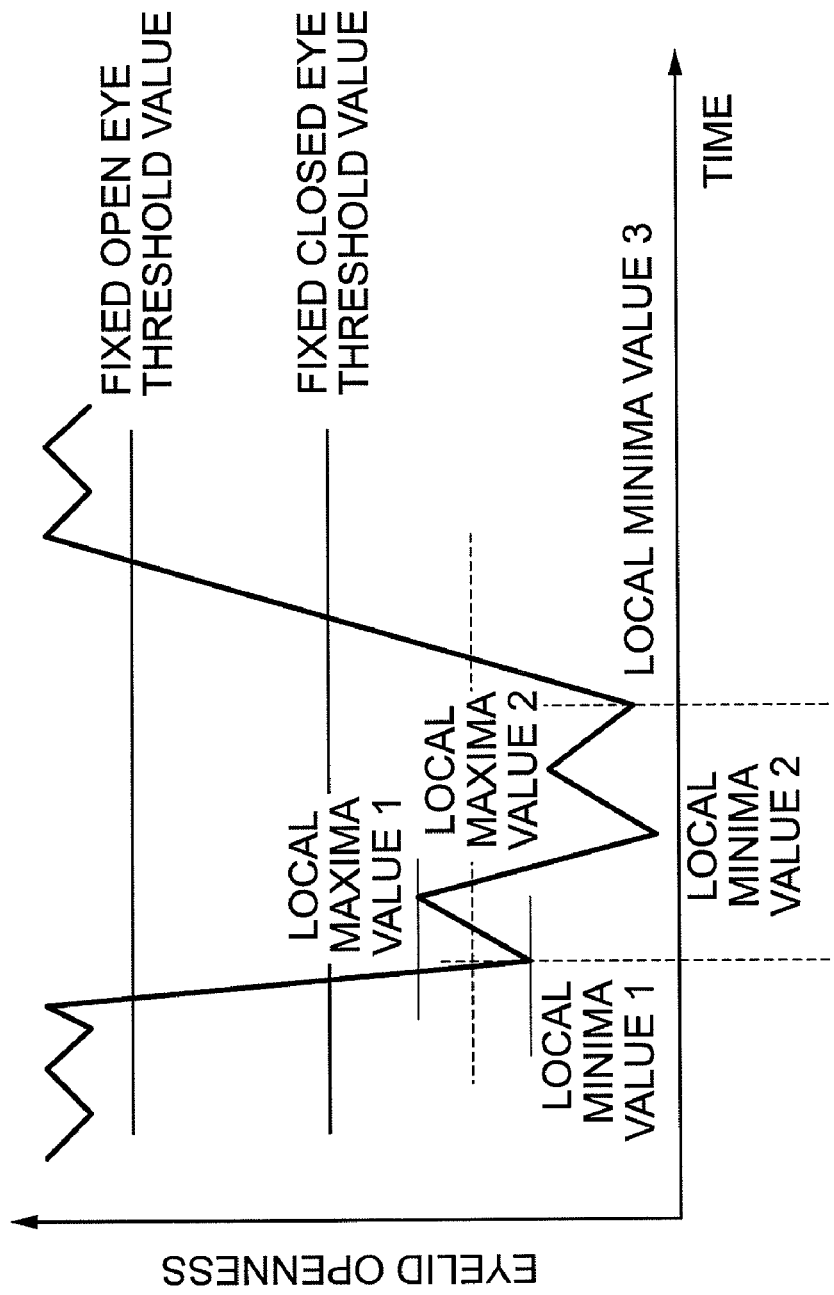
FIG. 3 is a graph illustrating local maxima values and local minima values in eyelid openness time series data.

As shown in FIG. 3, when blinks are buried under a given threshold value and cannot be separate out, a lower threshold value than the fixed closed eye threshold value needs to be set in order to detect blink bursts. The second blink burst detection section 30 accordingly performs blink burst detection as per the following explanation.

The second blink burst detection section 30 first, similarly to the first blink burst detection section 28, extracts blinks from the open or closed eye state time series data determined using the fixed closed eye threshold value and the fixed open eye threshold value. When an extracted continuous closed eye period of blinking is 1 second as a second specific time duration or longer, the second blink burst detection section 30 derives local maxima values and local minima values (for example by deriving points at the change in direction indicated by the derivatives) included in such a continuous closed eye period segment (a range in which the eyelid openness continues at the fixed closed eye threshold value or less for a range of 1 second or longer) in the eyelid openness time series data.

When there are plural local minima values in a segment of a continuous closed eye period of the specific time duration (for example 1 second) or greater, the second blink burst detection section 30 extracts blinks passing over and back through each variable closed eye threshold value of a variable closed eye threshold that is slid in a direction from the derived local maxima value (see the local maxima value 1 of FIG. 3) towards the local minima value (see the local minima value 1 of FIG. 3) in set steps to a low value, and an inter-blink interval is derived.

Determination that a blink burst has occurred is made when the derived inter-blink interval is the specific time duration or less (for example 1 second or less), and is 0.2 seconds or greater, with a blink burst accordingly detected.

When a continuous closed eye period is a long blink the second blink burst detection section 30 thereby sets a variable closed eye threshold value lower than the fixed closed eye threshold value and performs blink burst detection in the segment of the inter-blink interval.

The percentage closed eye extraction section 32 extracts a percentage closed eye (Perclos) that is the proportion of closed eye in a specific period of time from the open or closed eye state time series data determined using the fixed closed eye threshold value and the fixed open eye threshold value.

The drowsiness assessment section 34 performs threshold value determination on the extracted percentage closed eye, and assesses that the driver subject to assessment is in a strong state of drowsiness when the percentage closed eye is a threshold value related to percentage closed eye or greater. The drowsiness assessment section 34 also assesses that the driver subject to assessment is in a strong state of drowsiness when at least one of the first blink burst detection section 28 and/or the second blink burst detection section 30 has detected a blink burst.

Figure 4:
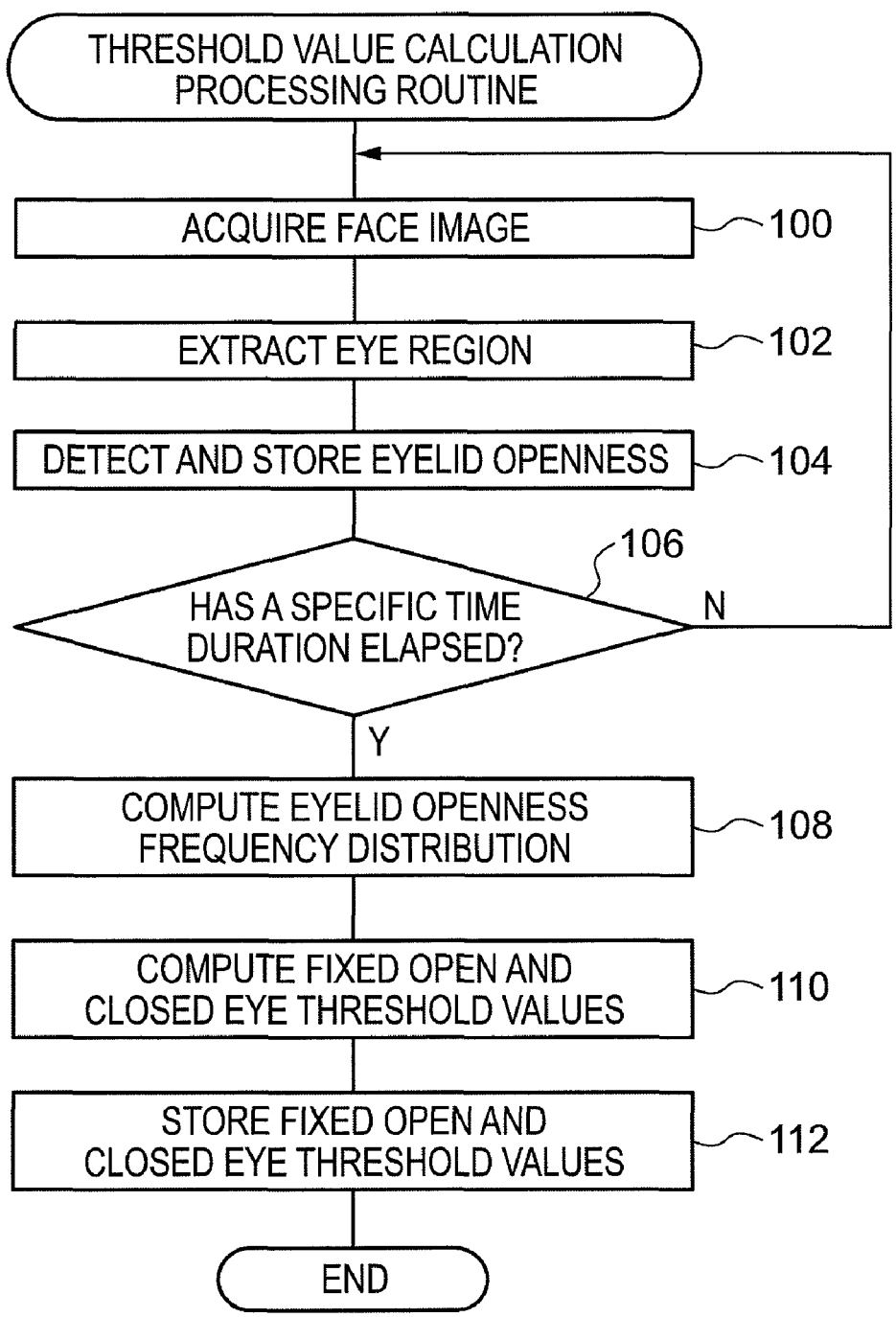
FIG. 4 is a flow chart showing contents of a threshold value calculation processing routine in a computer of a drowsiness assessment device according to the first exemplary embodiment of the present invention.

Explanation follows regarding operation of the drowsiness assessment device 10 according to the present exemplary embodiment. First successive images are captured of the face of a driver with the image capture device 12 and then the computer 20 executes the threshold value calculation processing routine shown in FIG. 4.

At step 100 the face image is acquired from the image capture device 12, and at step 102 an eye region is extracted from the acquired face image.

Then at step 104 eyelid openness is computed based on the image of the extracted eye region and stored in the memory (not shown in the drawings). Then at step 106 determination is made as to whether or not a specific time duration has elapsed since the start of processing. Processing returns to step 100 when the specific time duration has not yet elapsed, however processing proceeds to step 108 when the specific time duration has elapsed.

Time series data of eyelid openness detected during the specific time duration is stored in the memory by the above step 100 to step 106.

At step 108 an eyelid openness frequency distribution is computed from the eyelid openness time series data stored in the memory. The eyelid openness frequency distribution computed at step 108 is then employed in step 110 to compute a standard fixed open eye threshold value and a fixed closed eye threshold value, respectively.

At step 112 the fixed open eye threshold value and the fixed closed eye threshold value computed at step 110 are stored in the memory, thereby completing the threshold value calculation processing routine.

Figure 5:
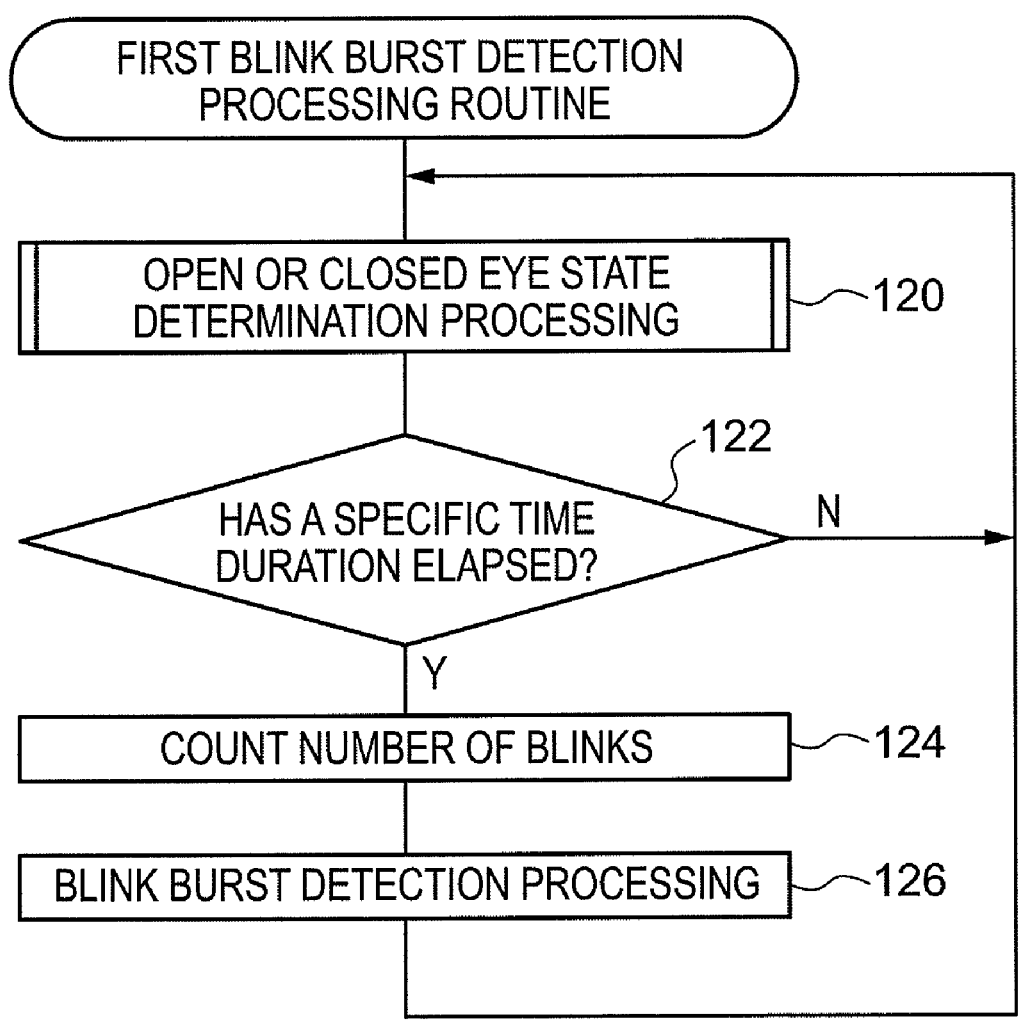
FIG. 5 is a flow chart showing contents of a first blink burst detection processing routine in a computer of a drowsiness assessment device according to the first exemplary embodiment.

When the fixed open eye threshold value and the fixed closed eye threshold value have first been calculated by the above threshold value calculation processing routine and successive images of the face of a driver have been captured by the image capture device 12, a first blink burst detection processing routine as illustrated in FIG. 5 is executed by the computer 20.

Figure 6:
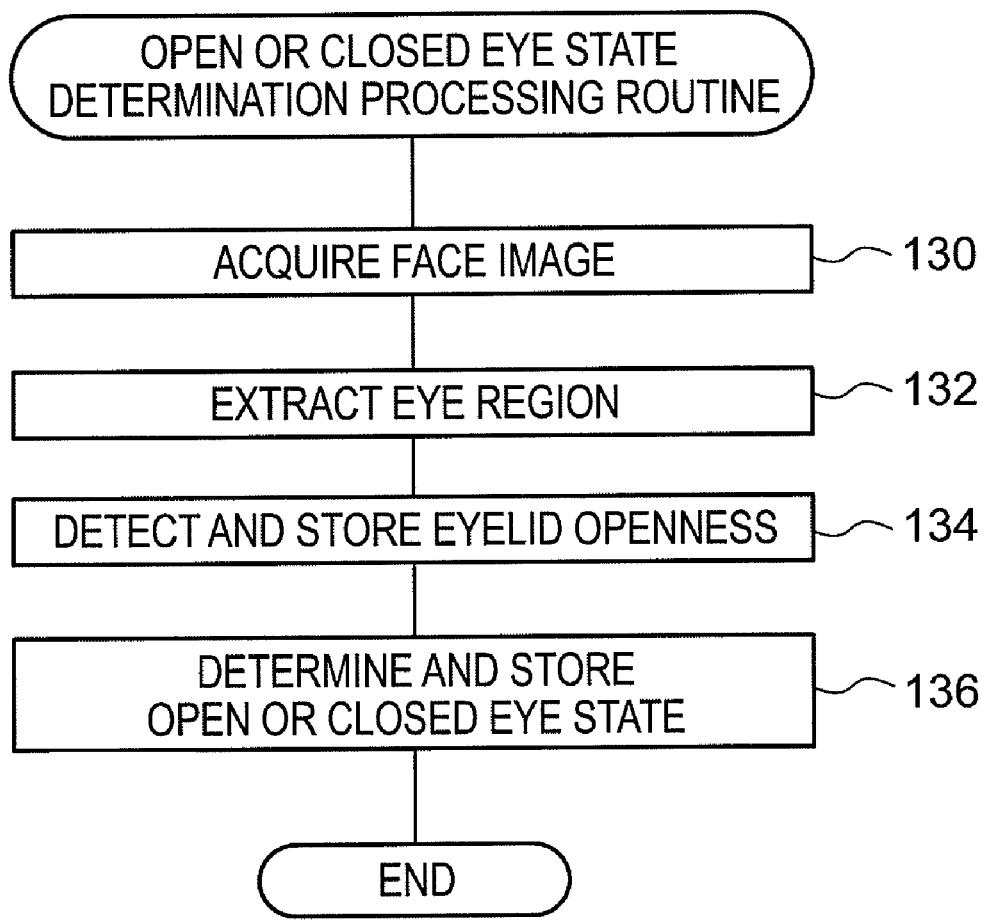
FIG. 6 is a flow chart showing contents of an open or closed eye state determination processing routine in a computer of a drowsiness assessment device according to the first exemplary embodiment of the present invention.

Open or closed eye state determination processing is performed at step 120. Step 120 is realized by the open or closed eye state determination processing routine shown in FIG. 6.

At step 130 a face image is acquired from the image capture device 12 and an eye region is extracted from the face image at step 132. Then at step 134 the eyelid openness is detected based on the extracted image of the eye region and stored in a memory (not shown in the drawings). Then in step 136 the eyelid openness detected at step 134 is compared with each of the fixed open eye threshold value and the fixed closed eye threshold value, and the open or closed eye state determined and stored in the memory (not shown in the drawings), thereby completing the open or closed eye state determination processing routine.

Then at step 122 of the first blink burst detection processing routine determination is made as to whether or not a specific time duration (for example 10 seconds) has elapsed since the start of processing. Processing returns to step 120 when the specific time duration has not yet elapsed and processing proceeds to step 124 when the specific time duration has elapsed. By this time both the eyelid openness time series data and the open or closed eye state time series data for the specific time duration are stored.

At step 124 the number of blinks is counted in the open or closed eye state time series data stored at step 120. At step 126 blink bursts are detected by determining whether or not the number of blinks within a fixed period of time (say 1 second) is a specific value or greater based on the number of blinks counted at step 124, and then processing returns to step 120.

Figure 7:
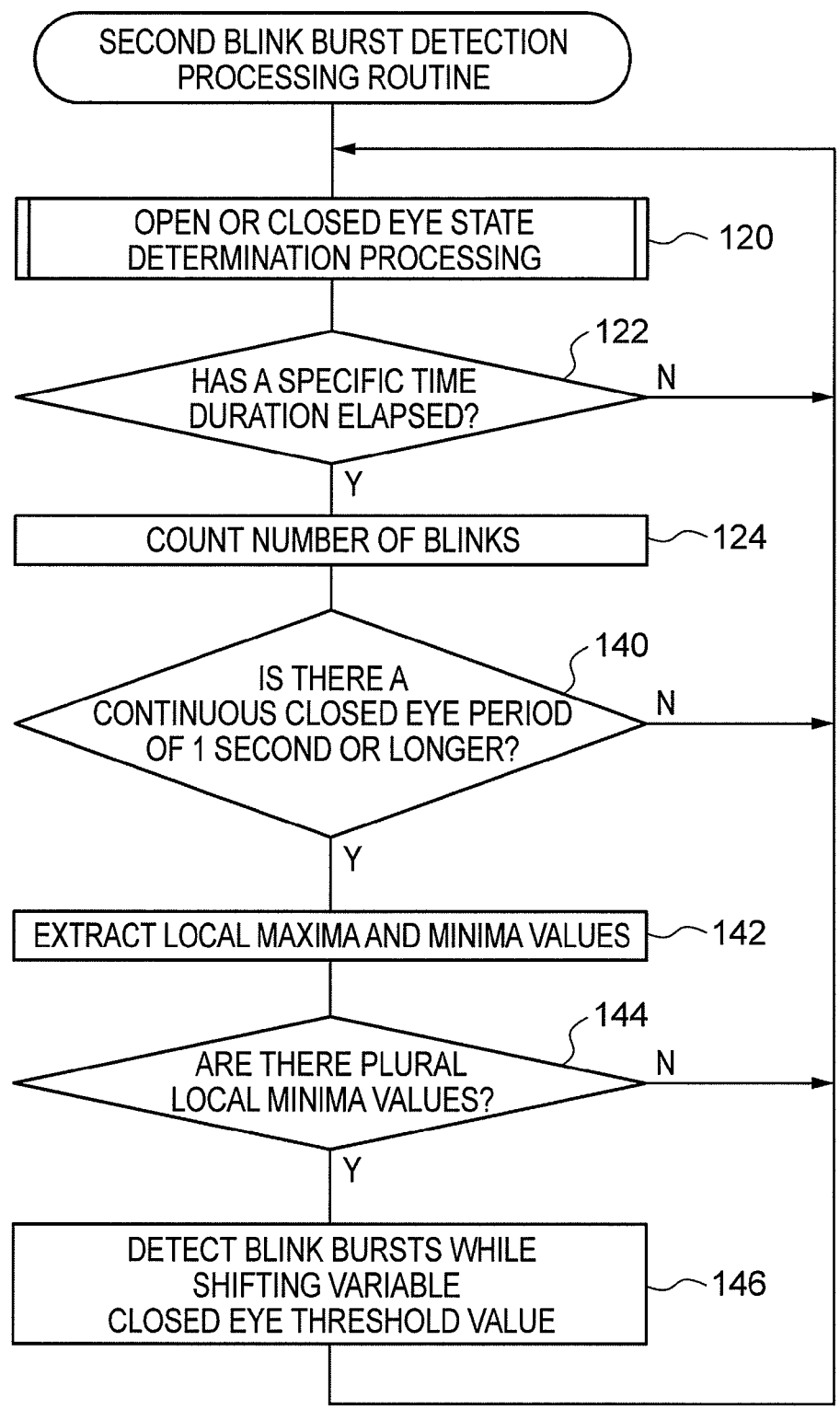
FIG. 7 is a flow chart showing contents of a second blink burst detection processing routine in a computer of a drowsiness assessment device according to the first exemplary embodiment of the present invention.

The computer 20 also executes the second blink burst detection processing routine as shown in FIG. 7. Open or closed eye state determination processing is first performed at step 120. Then at 122 determination is made as to whether or not a specific time duration (say 10 seconds) has elapsed since the start of processing. Processing returns to step 120 when the specific time duration has not yet elapsed and processing proceeds to step 124 when the specific time duration has elapsed. At step 124 the number of blinks is counted in the open or closed eye state time series data stored at step 120. The processing of steps 120 to 124 is similar to that of the first blink burst detection processing routine and may be configured as common processing.

Then at step 140 determination is made as to whether or not there is a continuous closed eye period of a specific time duration (say 1 second) or longer based on the number of blinks counted at step 124. Determination is made that no blink burst has occurred when there is no continuous closed eye period of the specific time duration (say 1 second) or longer present in the counted blinks and processing returns to step 120. However, when there is a continuous closed eye period present of the specific time duration (say 1 second) or longer then local maxima value(s) and local minima value(s) are extracted at step 142 from the eyelid openness time series data in the segment of the continuous closed eye period of 1 second or greater in the eyelid openness time series data stored at step 120.

Then at step 144 determination is made as to whether or not there are plural local minima values extracted at step 142. When plural local minima values were not extracted then determination is made that blink burst has not occurred and processing returns to step 120. However, when plural local minima values were extracted from the eyelid openness time series data in the segment of continuous closed eye period of 1 second or longer then at step 146 a variable closed eye threshold value is provided while sliding the variable closed eye threshold value in a direction from the extracted local maxima value towards the local minima value, and blinks are exacted for each of the variable closed eye threshold values and the inter-blink interval is derived. Determination is made that blink burst has occurred when the inter-blink interval is, for example, from 0.2 seconds to 1 second, accordingly detecting a blink burst. Processing returns to step 120 when blink burst detection has been performed in this manner.

Figure 8:
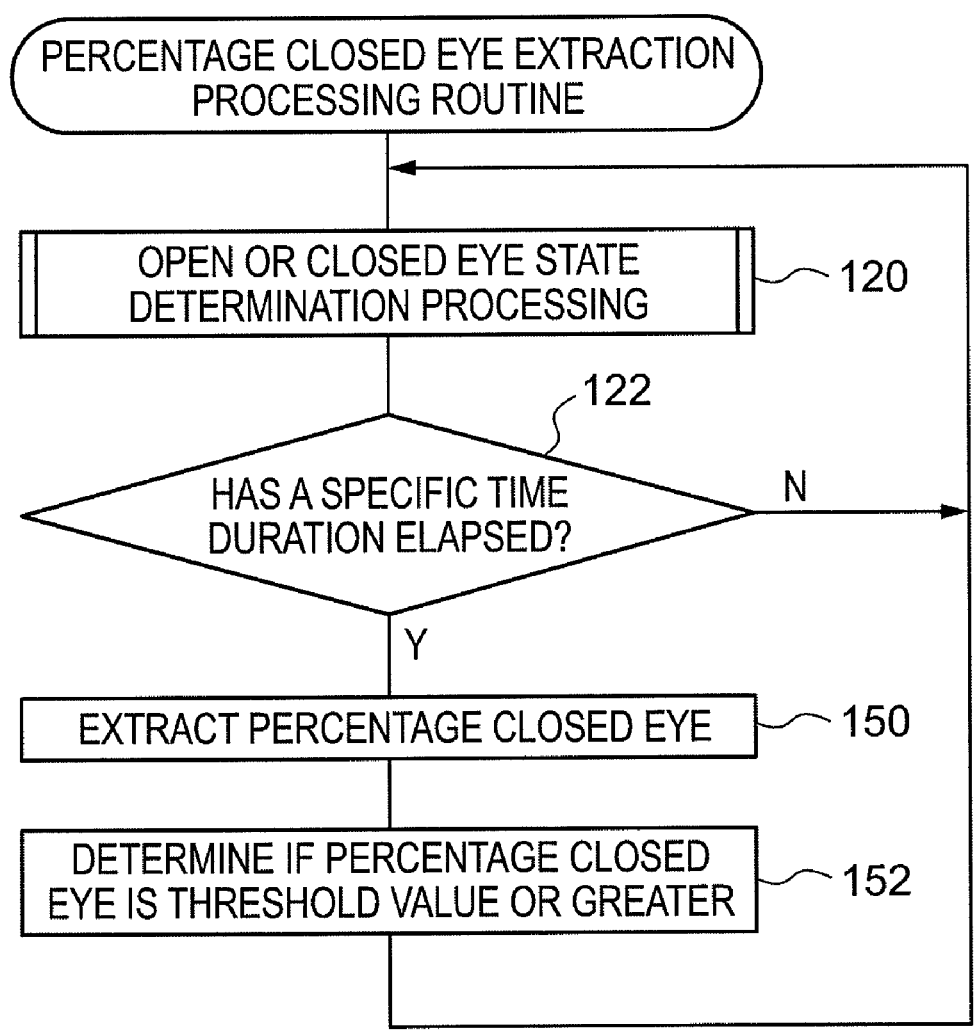
FIG. 8 is a flow chart showing contents of a percentage closed eye extraction processing routine in a computer of a drowsiness assessment device according to the first exemplary embodiment of the present invention.

A percentage closed eye extraction processing routine as shown in FIG. 8 is also executed in the computer 20. First open or closed eye state determination processing is performed at step 120. Then, at 122 determination is made as to whether or not a specific time duration (say 10 seconds) has elapsed since the start of processing. Processing returns to step 120 the specific time duration has not yet elapsed and processing transitions to step 150 when the specific time duration has elapsed. The processing of steps 120, 122 is similar to that of the first blink burst detection processing routine and may be configured as common processing.

At step 150 the percentage closed eye is extracted from the open or closed eye state time series data stored at step 120. Then at step 152 threshold value determination is performed on the percentage closed eye extracted at step 150, thereby determining whether or not the percentage closed eye is a determined threshold value or greater, with processing then returning to step 120.

By executing each of the first blink burst detection processing routine, the second blink burst detection processing routine and the percentage closed eye extraction processing routine as described above, the computer 20 acquires the blink burst detection result of the first blink burst detection processing routine, the blink burst detection result of the second blink burst detection processing routine, and the result of threshold value determination of the percentage closed eye extraction processing routine. The computer 20 assesses that the driver is in a strong state of drowsiness when blink burst has been detected and/or when the percentage closed eye is the percentage closed eye related threshold value or greater, and then displays a warning message on the display device 40 prompting the driver to pay attention to drowsiness.

As explained above, according to a drowsiness assessment device of the first exemplary embodiment, local maxima value(s) and local minima value(s) are extracted from eyelid openness time series data over the range of a closed eye state where the eyelid openness is continuously maintained at less than a fixed closed eye threshold value, and then blink bursts are detected by employing a variable closed eye threshold value provided between the local maxima value and the local minima value. Blink bursts can accordingly be detected with good precision, and the state of drowsiness can be assessed with good precision. This enables the phenomenon of blinking occurring in bursts to be detected without fail in eyelid openness time series data, and as a result improved assessment of the state of drowsiness of a driver can be achieved.

In the present exemplary embodiment the blink bursts are split into two types and each are detected by a different method. One of these types is blink burst with comparatively large repeated changes of eyelid openness between the open eye state and the closed eye state, with these blink bursts extracted by a method that counts the number of times passing over and back through a fixed closed eye threshold value. The other of these types is blink bursts with repeated tiny changes in state in the vicinity of the closed eye state, with these blink bursts extracted by a method that counts the number of times passing over and back through a variable closed eye threshold value for detection, provided below the closed eye threshold value between the local maxima value and the local minima value. Blink bursts can accordingly be detected with good precision as indicators for drowsiness assessment.

Explanation follows regarding a second exemplary embodiment. Since the configuration of a drowsiness assessment device according to the second exemplary embodiment is similar to the configuration of the drowsiness assessment device according to the first exemplary embodiment the same reference numerals are allocated and further explanation thereof is omitted.

The second exemplary embodiment differs from the first exemplary embodiment in that blinks are extracted while changing a variable closed eye threshold value from each of plural extraction segments determined with the minimum unit of time in a segment where there is a continuous closed eye period of a specific time duration (say 1 second) or longer and blink bursts are detected.

A second blink burst detection section 30 of the drowsiness assessment device according to the second exemplary embodiment performs blink burst detection as explained below.

The second blink burst detection section 30 first, similarly to the first blink burst detection section 28, extracts blinks from open or closed eye state time series data determined using a fixed closed eye threshold value and a fixed open eye threshold value. When an extracted blink occurs for a continuous closed eye period of a specific time duration (say 1 second) or longer, the second blink burst detection section 30, as shown in FIG. 9 sets plural extraction segments in such a segment, with each of the plural extraction segments having a set minimum unit of time.

The second blink burst detection section 30 then derives local maxima value(s) and local minima value(s) included in the extraction segments in the eyelid openness time series data for each of the set extraction segments. When there are plural local minima values present in the extraction segment, the second blink burst detection section 30 extracts blinks passing over and back through each variable closed eye threshold value of a variable closed eye threshold that is slid in a direction from the derived local maxima value towards the local minima value in set steps to a low value. The second blink burst detection section 30 derives an inter-blink interval for the extracted blinks, and determines that a blink burst has occurred when the derived inter-blink interval is, for example, from 0.2 seconds to 1 second, accordingly detecting a blink burst.

As explained above, the second blink burst detection section 30 performs blink burst detection for each of the extraction segments.

Figure 9:
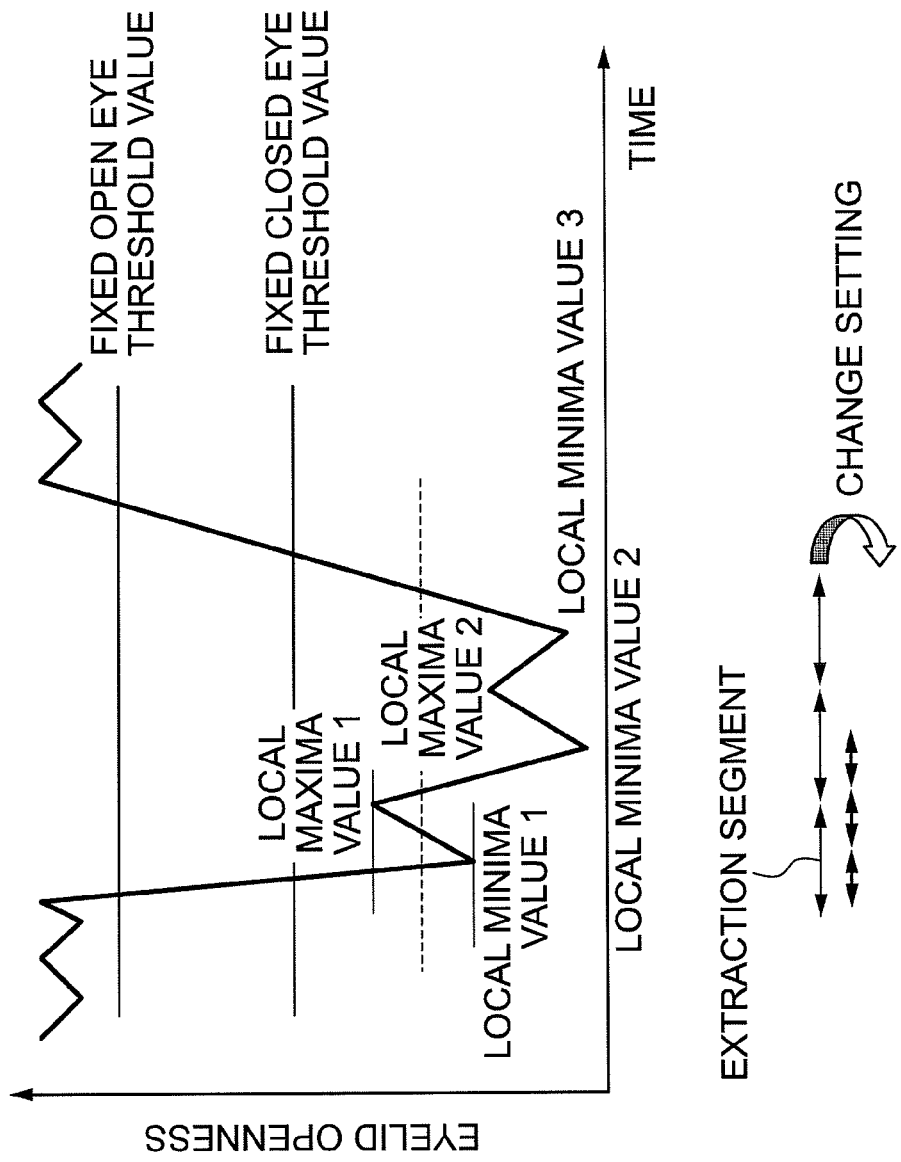
FIG. 9 is an image illustrating extraction segments set in a closed eye state segment.

A user can change the setting of the minimum unit time period by operating the computer 20, as shown in FIG. 9. The computation load can be adjusted by thereby changing the extraction segments for extracting maximum and minimum values.

Figure 10:
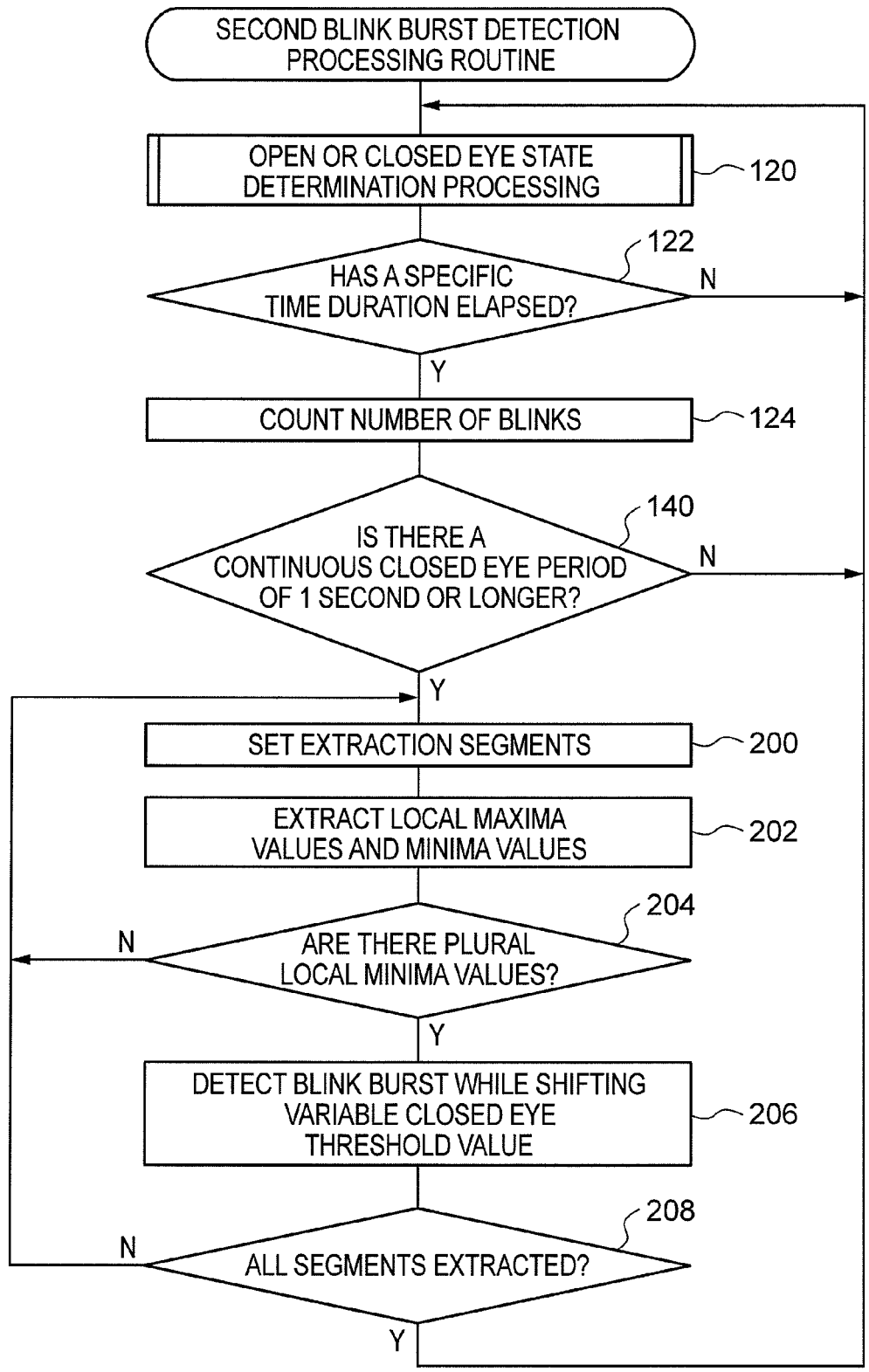
FIG. 10 is a flow chart showing contents of a second blink burst detection processing routine in a computer of a drowsiness assessment device according to a second exemplary embodiment of the present invention.

Explanation follows regarding operation of the second blink burst detection processing routine according to the second exemplary embodiment, with reference to FIG. 10. Processing similar to that of the first exemplary embodiment is allocated the same reference numerals and further detailed explanation is omitted.

First at step 120 open or closed eye state determination processing is performed. Then at step 122 determination is made as to whether or not a specific time duration has elapsed since the start of processing. Processing returns to step 120 when the specific time duration has not yet elapsed, however processing proceeds to step 124 when the specific time duration has elapsed. At step 124 the number of blinks is counted in the open or closed eye state time series data stored at step 120.

Then at step 140 determination is made as to whether or not there is a continuous closed eye period of a specific time duration (say 1 second) or longer. Determination is made that no blink burst has occurred when there is no continuous closed eye period present of the specific time duration (say 1 second) or longer in the counted blinks, with processing then returning to step 120. However, when there is a continuous closed eye period of the specific time duration (say 1 second) or longer present then at step 200 an extraction segment of a set minimum unit of time is set in the segment of the continuous closed eye period of 1 second or longer. At step 202 local maxima values and local minima values are extracted from the eyelid openness time series data in the extraction segments set in step 200 from out of the eyelid openness time series data stored at step 120.

Then in step 204 determination is made as to whether or not there have been plural local minima values extracted at step 202. Determination is made that blink burst has not occurred when plural local minima values have not been extracted, processing returns to step 200 and the extraction segment is shifted and set.

However, when plural local minima values have been extracted from the eyelid openness time series data for the extraction segment, a variable closed eye threshold value is slid in a direction from the extracted maximum value towards the local minima value and set at step 206, blinks are extracted for each of the variable closed eye threshold values, and an inter-blink interval derived. Determination is made that blink burst has occurred when the inter-blink interval is, for example, 0.2 seconds to 1 second, thereby detecting blink burst. When detection of blink burst has been performed in this manner processing proceeds to step 208 where determination is made as to whether or not the above extraction processing has been performed for all of the extraction segments set in the segment of continuous closed eye period of 1 second or longer. Processing returns to step 200 when the above processing has not yet been performed and the extraction segment is shifted and set. However, when determined that the above processing has already been performed for all of the extraction segments processing returns to step 120.

Since other parts of the configuration and operation of the drowsiness assessment device of the second exemplary embodiment are similar to that of the first exemplary embodiment further explanation is omitted.

Blink burst can be detected with good precision by setting plural extraction segments in the segment of continuous closed eye period of the specific time duration or longer, and setting the variable closed eye threshold value between the local maxima value and the local minima value for each of the extraction segments one at a time, as described above.

Explanation follows regarding a third exemplary embodiment. The configuration of the drowsiness assessment device of the third exemplary embodiment is similar to the configuration of the drowsiness assessment device according to the first exemplary embodiment and so the same reference numerals are allocated and further explanation thereof is omitted.

The third exemplary embodiment differs from the first exemplary embodiment in that blink bursts are detected based on an interval between local minima values in a segment of continuous closed eye period of a specific time duration (say 1 second) or longer.

The second blink burst detection section 30 of the drowsiness assessment device according to the third exemplary embodiment performs blink burst detection as described in the following.

First the second blink burst detection section 30, similarly to the first blink burst detection section 28, extracts blinks from open or closed eye state time series data determined using a fixed closed eye threshold value and a fixed open eye threshold value. When there is a continuous closed eye period of the extracted blinks of a specific time duration (say 1 second) or longer, the second blink burst detection section 30 derives local minima value(s) contained in the segment of continuous closed eye period.

When there are plural local minima values present in the segment of continuous closed eye period of the specific time duration (say 1 second) or longer, the second blink burst detection section 30 derives the interval between the local minima values. The second blink burst detection section 30 determines that blink burst has occurred when the derived interval between the local minima values is, for example, from 0.2 seconds to 1 second, thereby detecting blink burst.

Accordingly, when the continuous closed eye period has long blinking, the second blink burst detection section 30 performs blink burst detection based on the interval between local minima values in the segment of the continuous closed eye period.

Figure 11:
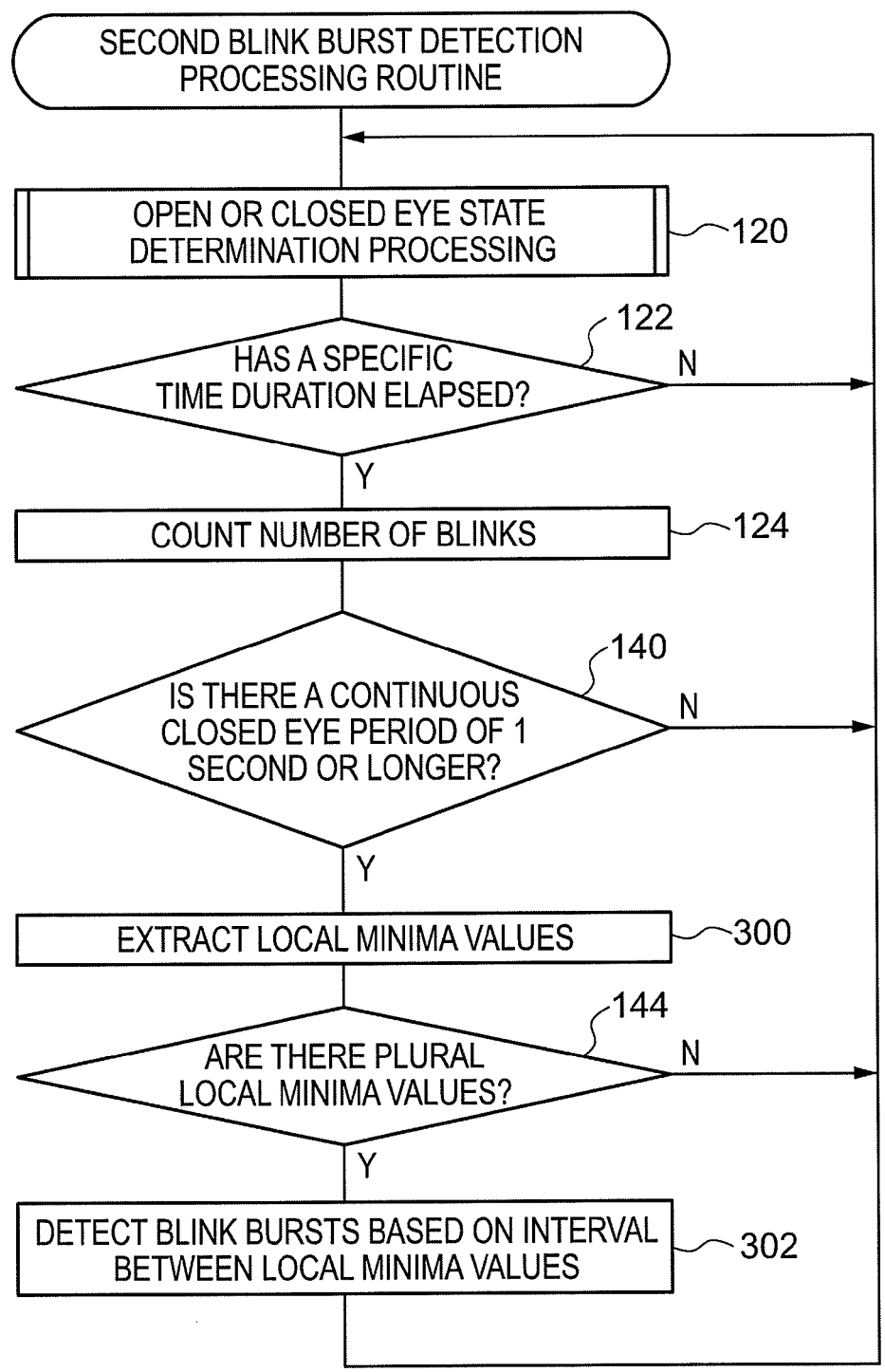
FIG. 11 is a flow chart showing contents of a second blink burst detection processing routine in a computer of a drowsiness assessment device according to a third exemplary embodiment of the present invention.

Explanation follows regarding a second blink burst detection processing routine according to the third exemplary embodiment, with reference to FIG. 11. Similar processing to that of the first exemplary embodiment is allocated the same reference numerals and further explanation is omitted.

First open or closed eye state determination processing is performed at step 120. Then at 122 determination is made as to whether or not a specific time duration has already elapsed since the start of processing. Processing returns to step 120 when the specific time duration has not yet elapsed, however processing proceeds to step 124 when the specific time duration has elapsed. At step 124 the number of blinks is counted in the open or closed eye state time series data stored at step 120. Then at step 140 determination is made as to whether or not there is a continuous closed eye period of a specific time duration (say 1 second) of longer. Determination is that a blink burst has not occurred when there is no continuous closed eye period present of the specific time duration (say 1 second) or longer, with processing returning to step 120.

However, when there is a continuous closed eye period present of the specific time duration (say 1 second) or longer, then at step 300 local minima value(s) are extracted from the eyelid openness time series data in the segment of the continuous closed eye period of 1 second or longer in the eyelid openness time series data stored at step 120.

At step 144 determination is made as to whether or not plural local minima values have been extracted at step 300. Determination is that blink burst has not occurred when plural local minima values were not extracted, and processing returns to step 120. However, when plural local minima values were extracted from the eyelid openness time series data in the segment of 1 second or longer, then the interval between the extracted local minima values is derived at step 302. Blink burst is determined to have occurred with the interval between local minima values is, for example, from 0.2 seconds to 1 second, and blink burst is accordingly detected. Processing returns to step 120 when detection of blink burst has been performed as described above.

Since other parts of the configuration and operation of the drowsiness assessment device according to the third exemplary embodiment are similar to those of the first exemplary embodiment further explanation is omitted.

Local minima values are extracted from eyelid openness time series data in the range in which the eyelid openness is less than the fixed closed eye threshold value, and blink bursts are detected based on the interval between the extracted local minima values. The blink bursts can accordingly be detected with good precision and the state of drowsiness can also be assessed with good precision.

Explanation follows regarding a fourth exemplary embodiment. The configuration of a drowsiness assessment device according to the fourth exemplary embodiment is similar to the configuration of the drowsiness assessment device of the first exemplary embodiment and so the same reference numerals are allocated and further explanation is omitted.

The fourth exemplary embodiment differs from the first exemplary embodiment in that local maxima values and local minima values are derived only after noise has been separated from the eyelid openness time series data using an envelope curve.

Figure 12:
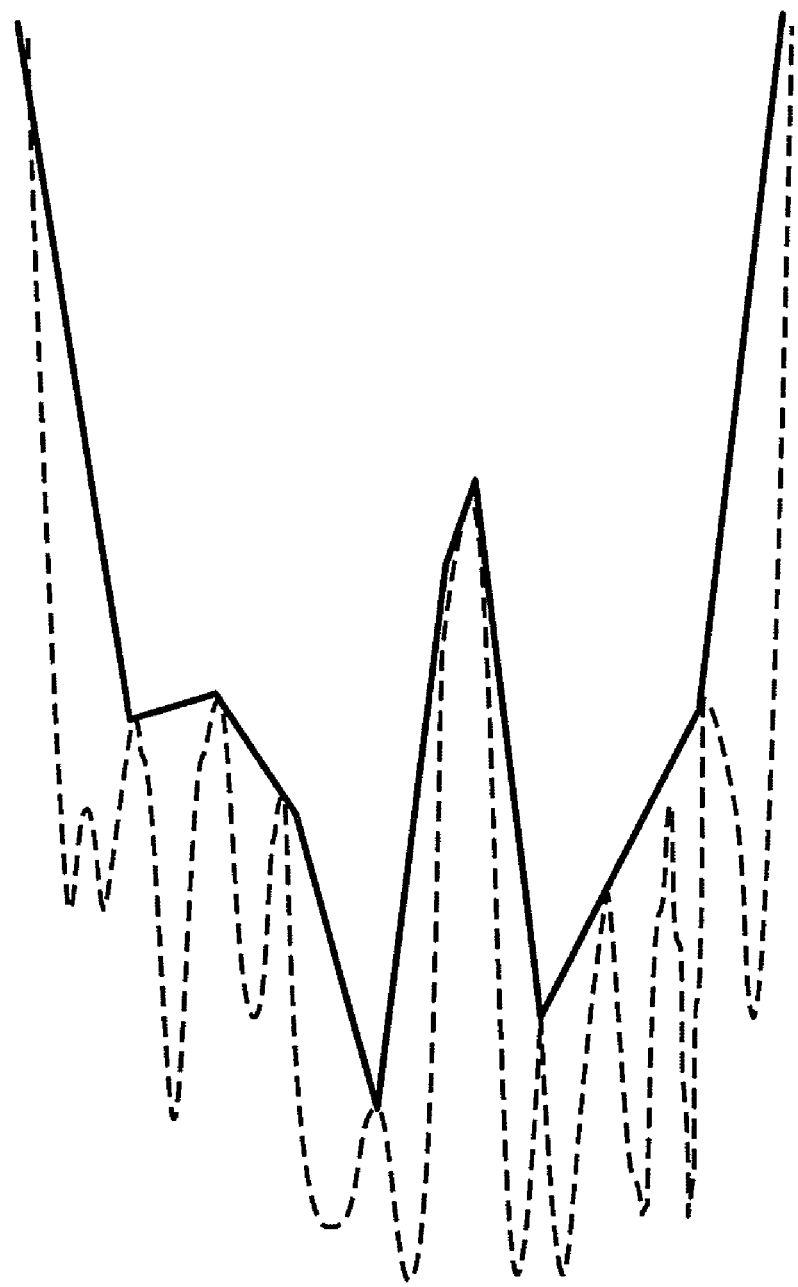
FIG. 12 is a graph illustrating an envelope curve in eyelid openness time series data.

A second blink burst detection section 30 of a drowsiness assessment device according to the fourth exemplary embodiment extracts blinks from the open or closed eye state time series data determined using the fixed closed eye threshold value and the fixed open eye threshold value. When there is a continuous closed eye period of extracted blinks of a specific time duration (say 1 second) or longer, the second blink burst detection section 30 separates out noise from the eyelid openness time series data in the continuous closed eye period segment using an envelope curve like the one shown in FIG. 12. The second blink burst detection section 30 then derives local maxima values and local minima values contained in the segment from the envelope curve of the eyelid openness time series data in the continuous closed eye period segment. The second blink burst detection section 30 employs the derived local maxima value(s) and local minima value(s), provides variable closed eye threshold provided while sliding the variable closed eye threshold, extracts blinks passing over and back through each value of a variable closed eye threshold, and derives the inter-blink interval. The second blink burst detection section 30 detects blink bursts based on the derived inter-blink interval.

Since other parts of the configuration and operation of the drowsiness assessment device according to the fourth exemplary embodiment are similar to those of the first exemplary embodiment further explanation will be omitted.

By separating out noise from the eyelid openness time series data using an envelope curve any local maxima values and the local minima values due to noise can be separated out. Accordingly blink bursts can be detected with good precision.

While explanation has been given of examples in the above first to fourth exemplary embodiments where percentage closed eye is extracted as a blink characteristic amount and then threshold value determination is performed thereon, there is no limited thereto. Configuration may be made with the maximum closed eye duration, the number of blinks, a variance of open eye duration, and/or the maximum open eye duration extracted and threshold value determination performed thereon.

Furthermore, while explanation has been given of examples of determining the presence or absence of blink bursts, there is no limitation thereto. Configuration may be made such that the number of times blink bursts occur is also measured as well as the presence or absence of blink bursts being determined. In such cases configuration may be made such that the blink burst rate (the number of times blink bursts occur in a given unit of time) is detected from the number of blink bursts.

A program according to the present invention may be provided stored on a storage medium.

EXPLANATION OF THE REFERENCE NUMERALS

10 Drowsiness Assessment Device
12 IMAGE CAPTURE DEVICE
22 EYE REGION EXTRACTION SECTION
24 EYELID OPENNESS DETECTION SECTION
26 OPEN OR CLOSED EYE STATE DETERMINATION SECTION
28 FIRST BLINK BURST DETECTION SECTION
30 SECOND BLINK BURST DETECTION SECTION
32 PERCENTAGE CLOSED EYE EXTRACTION SECTION
34 DROWSINESS ASSESSMENT SECTION

The invention claimed is:

1. A drowsiness assessment device comprising:
   image capture section that successively captures an image of a region including an eye of an assessment subject;
   openness detection section that detects time series data of eyelid openness based on the images successively captured by the image capture section;
   blink burst detection section that based on the eyelid openness time series data detected by the openness detection section extracts any local maxima values and local minima values from a range in which the eyelid openness is continuously less than a predetermined threshold value and detects blink bursts when an inter-blink interval detected at a threshold value set between an extracted local maxima value and an extracted local minima value is within a specific time duration; and
   state of drowsiness assessment section that assesses the state of drowsiness of the assessment subject based on the detection result of the blink burst detection section.

2. The drowsiness assessment device of claim 1, wherein the predetermined threshold value is set as a standard closed eye threshold value related to eyelid openness.

3. The drowsiness assessment device of claim 1, wherein the blink burst detection section extracts any local maxima values and local minima values in a range of eyelid openness continuously less than the predetermined threshold value from a range of a second specific time duration or longer, and detects blink bursts when an inter-blink interval detected at a threshold value set between an extracted local maxima value and an extracted local minima value is within the specific time duration.

4. The drowsiness assessment device of claim 1, wherein the blink burst detection section extracts any local maxima values and local minima values respectively from a plurality of extraction sections obtained by dividing, at a minimum unit duration, a range of eyelid openness continuously less than the predetermined threshold value and detects blink bursts when an inter-blink interval detected at a threshold value set between an extracted local maxima value and an extracted local minima value is within the specific time duration.

5. A drowsiness assessment device comprising:
   image capture section that successively captures an image of a region including an eye of an assessment subject;
   openness detection section that detects time series data of eyelid openness based on the images successively captured by the image capture section;
   blink burst detection section that based on the eyelid openness time series data detected by the openness detection section extracts any local minima values from a range in which the eyelid openness is continuously less than a predetermined threshold value and detects blink bursts when an interval between extracted local minima values is within a specific time duration; and
   state of drowsiness assessment section that assesses the state of drowsiness of the assessment subject based on the detection result of the blink burst detection section.

6. The drowsiness assessment device of claim 1, further comprising second blink burst detection section that extracts blinks employing the predetermined threshold value based on the eyelid openness time series data detected by the openness detection section, and detects blink bursts based on the extracted blinks,
   wherein the state of drowsiness assessment section assesses the state of drowsiness of the assessment subject based on the detection result of the blink burst detection section and the detection result of the second blink burst detection section.

7. The drowsiness assessment device of claim 1, further comprising blink characteristic amount extraction section that extracts a blink characteristic amount different from blink bursts based on the eyelid openness time series data detected by the openness detection section,
   wherein the state of drowsiness assessment section assesses the state of drowsiness of the assessment subject based on the detection result of the blink burst detection means and based on the blink characteristic amount extracted by the blink characteristic amount extraction section.

8. A recording medium storing a computer program comprising instructions that are executable by a computer to function as:

openness detection section that detects time series data of eyelid openness based on images successively captured by an image capture section of a region including an eye of an assessment subject;

blink burst detection section that based on the eyelid openness time series data detected by the openness detection section extracts any local maxima values and local minima values from a range in which the eyelid openness is continuously less than a predetermined threshold value and detects blink bursts when an inter-blink interval detected at a threshold value set between an extracted local maxima value and an extracted local minima value is within a specific time duration; and state of drowsiness assessment section that assesses the state of drowsiness of the assessment subject based on the detection result of the blink burst detection section.

9. A recording medium storing a program causing a computer to function as functions comprising:

openness detection section that detects time series data of eyelid openness based on images successively captured by an image capture section of a region including an eye of an assessment subject;

blink burst detection section that based on the eyelid openness time series data detected by the openness detection section extracts any local minima values from a range in which the eyelid openness is continuously less than a predetermined threshold value and detects blink bursts when an interval between extracted local minima values is within a specific time duration; and state of drowsiness assessment section that assesses the state of drowsiness of the assessment subject based on the detection result of the blink burst detection section.

\* \* \* \* \*